(12) United States Patent
Hull

(10) Patent No.: US 7,658,729 B2
(45) Date of Patent: Feb. 9, 2010

(54) ATTACHMENT DEVICE AND SYSTEM FOR CORNEAL IRRIGATING CANNULA AND METHOD THEREOF

(76) Inventor: Thomas P. Hull, 3845 Yellow Creek West, Akron, OH (US) 44333

( * ) Notice: Subject to any disclaimer, the term of this patent is extended or adjusted under 35 U.S.C. 154(b) by 465 days.

(21) Appl. No.: 11/807,271

(22) Filed: May 25, 2007

(65) Prior Publication Data

US 2008/0289635 A1 Nov. 27, 2008

(51) Int. Cl.
*A61M 35/00* (2006.01)
(52) U.S. Cl. .................. 604/294; 604/295; 604/300
(58) Field of Classification Search .............. 604/294, 604/300–302, 236
See application file for complete search history.

(56) References Cited

U.S. PATENT DOCUMENTS 5,814,030 A * 9/1998 Hedges et al. ............... 604/294
6,733,128 B2 5/2004 Kirchhuebel

OTHER PUBLICATIONS

Gills, James P., M.D.; Strategies for Applying State of the Art Techniques; Chapter 18; pp. 229-234.

* cited by examiner

*Primary Examiner*—Nicholas D Lucchesi
*Assistant Examiner*—Leah Stohr
(74) *Attorney, Agent, or Firm*—Martin & Ferraro, LLP

(57) ABSTRACT

A cannula support serves in supporting a cannula relative to a non-contact lens assembly and a positioning mechanism for positioning the non-contact lens assembly. The cannula support includes a cannula holder and a gripper disposed relative to the cannula holder. The cannula holder is provided for receiving at least a portion of the cannula. The gripper is adapted to cooperatively engage a portion of one of the non-contact lens assembly and the positioning mechanism.

16 Claims, 3 Drawing Sheets

ATTACHMENT DEVICE AND SYSTEM FOR CORNEAL IRRIGATING CANNULA AND METHOD THEREOF

BACKGROUND OF THE INVENTION

1. Field of the Invention

The present invention relates generally to a eye surgery, and more particularly to surgical instrumentation and to a method for supporting a cannula relative to an eye in which the cannula can be actuated to irrigate the eye.

2. Description of the Prior Art

Traditionally, retinal surgeons relied on standard operating microscopes in conjunction with surgical contact lenses to view the interior of the eye. During use, the surgical contact lenses are held in place on the corneal surface of the eye. However, even though the surgical contact lenses provided a clear view of the interior of the eye, such lenses afforded only a limited field of view. Moreover, given that the surgical contact lenses must be held in place on the corneal surface, retinal surgeons were limited in their ability to manipulate the eye.

Binocular indirect ophthalmo microscopes (BIOMs) with wide-angle viewing systems are commonly employed by retinal surgeons during posterior segment eye surgery. BIOMs with wide-angle viewing systems offer superior functionality over standard operating microscopes used in conjunction with surgical contact lenses. BIOMs with wide-angle viewing systems allow for a greater field of view and increased surgical mobility. Rather than using surgical contact lenses, BIOMs with wide-angle viewing systems employ non-contact lens assemblies to view the interior of the eye. The non-contact lens assemblies include non-contact lenses positioned along the focal axes of the BIOMs. When focusing the BIOMs on the interior of the eye, the retinal surgeon adjusts and positions the non-contact lenses along the focal axes using positioning mechanisms.

To properly focus the BIOMs, the non-contact lenses must be positioned in close proximity to the eye. For example, the non-contact lenses are often positioned less than one inch from the corneal surface. During surgery, such close proximity to the corneal surface creates difficulties in keeping the corneal surface wet and consequently clear.

Typically, surgical assistants assist the retinal surgeons during surgery, and are charged with irrigating the eye. In doing so, the surgical assistants manually position and actuate a cannula to supply fluid to the eye. The close proximity of the non-contact lens to the eye can lead to unintentional wetting with fluid from the cannula when attempting to the irrigate the eye. Such unintentional wetting can delay the surgery until the non-contact lenses are cleaned or the non-contact lens assemblies are replaced. Moreover, because the surgical assistants must usually look up from oculars to manually position and actuate the cannula, there is also danger that manipulation of the cannula will deleteriously interfere with the surgery.

Therefore, there exists a need for surgical instrumentation and a method for supporting a cannula relative to an eye in which the cannula can be actuated to irrigate the eye, while inhibiting unintentional wetting of the non-contact lens and deleterious interference with the surgery.

SUMMARY OF THE INVENTION

The present invention in one preferred embodiment contemplates a cannula support for supporting a cannula relative to a non-contact lens assembly and a positioning mechanism for positioning the non-contact lens assembly, the cannula support includes a cannula holder, the cannula holder receiving at least a portion of the cannula, and a gripper disposed relative to the cannula holder, the gripper adapted to cooperatively engage a portion of one of the non-contact lens assembly and the positioning mechanism.

The present invention in a further preferred embodiment contemplates an irrigation system for irrigating an eye during surgery, the irrigation system includes a cannula, and a cannula support including a cannula holder, the cannula holder receiving at least a portion of the cannula, and a gripper disposed relative to the cannula holder, the gripper adapted to cooperatively engage a portion of one of a non-contact lens assembly and a positioning mechanism for positioning the non-contact lens assembly relative the eye, where the cannula can be actuated to release a supply of fluid.

The present invention in another preferred embodiment contemplates a positioning and irrigating system for use during eye surgery, the system includes a non-contact lens assembly, a positioning mechanism for positioning the non-contact lens assembly relative to the eye, a cannula, and a cannula support including a cannula holder, the cannula holder receiving at least a portion of the cannula, and a gripper disposed relative to the cannula holder, the gripper adapted to cooperatively engage a portion of one of the non-contact lens assembly and the positioning mechanism, where the cannula can be actuated to release a supply of fluid.

The present invention in yet another preferred embodiment contemplates a surgical microscope assembly for use during eye surgery including a surgical microscope having a focal axis, a non-contact lens assembly, a positioning mechanism for positioning the non-contact lens along the focal axis, a cannula, and a cannula support for supporting the cannula, the cannula support being attached to one of the non-contact lens assembly and the positioning mechanism.

The present invention also contemplates a method of irrigating an eye during eye surgery by providing a cannula support and a cannula having a tip, fixing the position of a portion of the cannula with the cannula support, positioning the tip of the cannula adjacent the eye, and actuating the cannula to provide a supply of fluid to the eye.

The present invention further contemplates a method of performing surgery on an eye by providing a surgical microscope having focal axis, positioning the eye along the focal axis, positioning a non-contact lens assembly between the eye and the surgical microscope, adjusting the position of the non-contact lens assembly along the focal axis to focus the surgical microscope on the eye, providing a cannula support, fixing the position of a portion of a cannula adjacent the eye using the cannula support, and actuating the cannula to irrigate the eye with a supply of fluid.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The following description is intended to be representative only and not limiting and many variations can be anticipated according to these teachings. Reference will now be made in detail to the preferred embodiments of this invention, examples of which are illustrated in the accompanying drawings.

Figure 1:
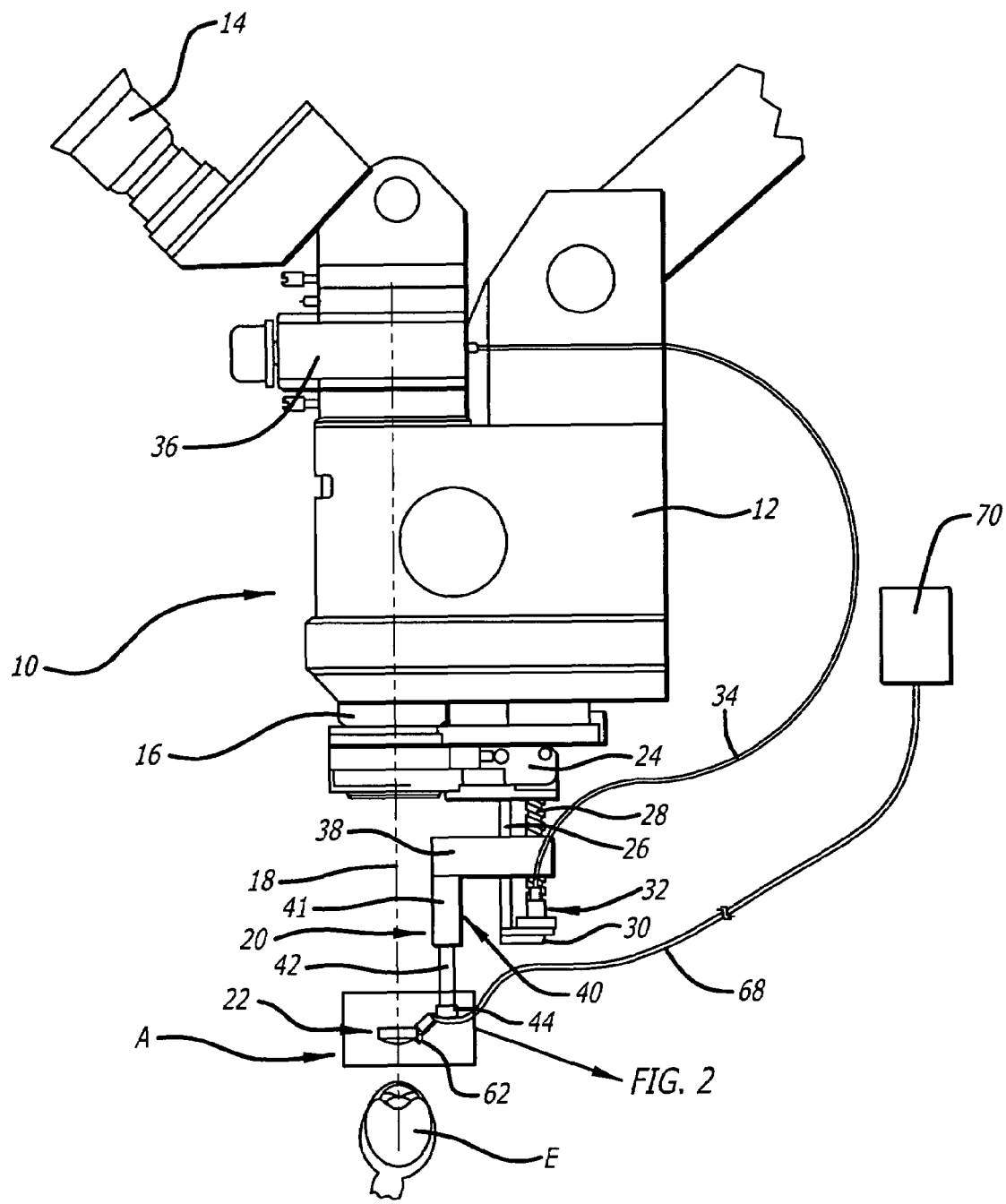
FIG. 1 is a side elevational view of a surgical microscope system positioned relative to an eye including a cannula support of the present invention.

FIG. 1 shows a surgical microscope 10 used by an ophthalmologist in performing eye surgery. Surgical microscope 10 includes a housing 12, an ocular 14, and a lens 16. Lens 16 includes a vertically-oriented optic axis 18 extending through a surgery area A. A patient is disposed in surgery area A, and, for illustrative purposes, a patient's eye E is shown in FIG. 1.

A positioning assembly 20 is attached adjacent lens 16. Positioning assembly 20 serves in positioning a non-contact lens assembly 22 relative to surgical microscope 10. Non-contact lens assembly 22 includes a non-contact lens B adapted to be positioned along optic axis 18. Using positioning assembly 20, non-contact lens assembly 22 is capable of vertical reciprocal movement relative lens 16 along optic axis 18. In doing so, non-contact lens B can be positioned in various vertical positions along optic axis 18 to focus surgical microscope 10.

Positioning assembly 20 includes a support arm 24 attached to housing 12 adjacent lens 16. Support arm 24 supports the remainder of positioning assembly 20, and can be rotated relative to housing 12 to swing non-contact lens assembly 22 into and out of position relative to optic axis 18. Support arm 24 is detachable from housing 12. A guide 26 and a spindle 28 extend downwardly from support arm 24. Guide 26 is a cylindrical rod, and spindle 28 is a threaded cylindrical rod. A stationary plate 30, oppositely disposed from support arm 24, is attached to guide 26 and spindle 28. Guide 26 fixedly attaches stationary plate 30 to support arm 24, and spindle 28 is rotatable between support arm 24 and stationary plate 30. Stationary plate 30 supports an actuation mechanism 32 used in rotating spindle 28.

Actuation mechanism 32 operatively engages spindle 28 to provide for rotation thereof. Gears or belts and pulleys can, for example, be used to operatively connect actuation mechanism 32 to spindle 28. Furthermore, actuation mechanism 32 is motivated by a drive shaft 34 extending downwardly from a drive mechanism 36. As shown in FIG. 1, drive mechanism 36 is positioned on housing 12 away from surgery area A. When actuated, rotary movement is transferred from drive mechanism 36 through drive shaft 36 to actuation mechanism 32. In turn, actuation mechanism 32 using the above-referenced gears or belts and pulleys serves to rotate spindle 28.

A movable plate 38 is adapted to receive guide 26 and spindle 28 therethrough. Movable plate 38 is slidable along guide 26, and threadingly engages spindle 28. Rotational movement of spindle 28 serves in repositioning movable plate 38 along guide 26 and spindle 28. As such, movable plate 38 is reciprocally moveable along guide 26 and spindle 28. Depending on whether spindle 28 is rotated clockwise or counter-clockwise, movable plate 38 is moved in vertical directions relative to surgical microscope 10 and patient's eye E.

A telescoping support tube 40 having a first portion 41 and a second portion 42 depends downwardly from moveable plate 38. First portion 41 is fixedly attached to moveable plate 38, and second portion 42 is moveable in and out of first portion 41. The movement of second portion 42 relative to first portion 41 occurs vertically relative to surgical microscope 10 and patient's eye E.

Non-contact lens assembly 22 is supported on second portion 42 of telescoping support tube 40. Second portion 42 includes a coupler 44 to which non-contact lens assembly 22 can be attached. Coupler 44 is adapted to allow non-contact lens assembly 22 to be detachable therefrom. As such, a variety of mechanical fasteners can be used for coupler 44. Being detachable allows non-contact lens assembly 22 to be interchangeable. As such, non-contact lens assembly 22 can be exchanged with other non-contact lens assemblies having non-contact lenses with different focal lengths. Therefore, depending on the characteristics of patient's eye E, a non-contact lens B with an appropriate focal length can be provided.

Figure 2:
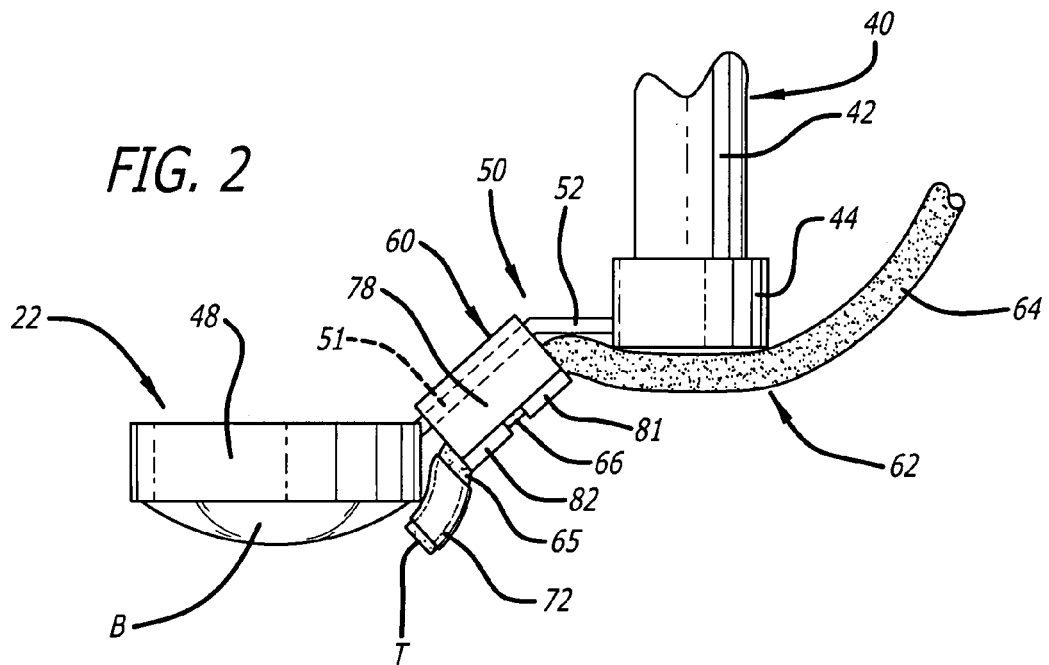
FIG. 2 is an enlarged side elevational view of FIG. 1 showing the cannula support attached to a non-contact lens assembly.
Figure 3:
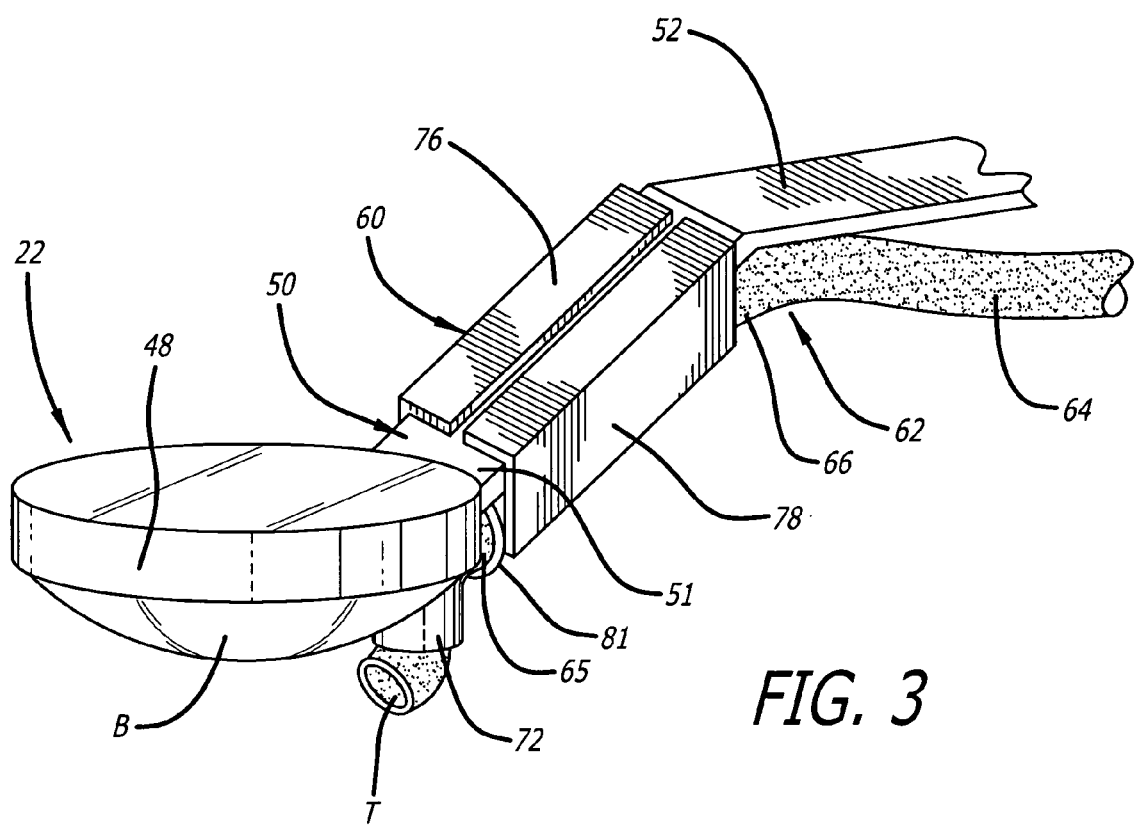
FIG. 3 is a perspective view of the cannula support shown in FIGS. 1 and 2 attached to the non-contact lens assembly.

In addition to non-contact lens B, non-contact lens assembly 22, as shown in FIGS. 2 and 3, includes a flange 48 and a stem 50. Flange 48 holds non-contact lens B, and stem 50 includes a first portion 51 and a second portion 52. First portion 51 extends outwardly from flange 48, and second portion 52 is adapted to be attached to coupler 44. The length and angle of first portion 51 are provided so that, when positioning assembly 20 is properly positioned relative to surgical microscope 10 and patient's eye E, optic axis 18 of surgical microscope 10 passes through non-contact lens B.

FIGS. 2 and 3 show a cannula support 60 supporting a cannula 62 attached to stem 50. Cannula 62 includes a proximal end portion 64, a distal end portion 65, and an intermediate portion 66 extending therebetween. Proximal end portion 64 is connected to a supply line 68 fluidly communicating with a reservoir 70, and distal end portion 65 includes a tip T. Tip T can be formed at a perpendicular angle or a non-perpendicular angle to the remainder of cannula 62. As such, tip T can be formed at an angle such that it is oriented away from non-contact lens assembly 22.

Cannula 62 is formed from flexible tubing made from, for example, silicon, vinyl, or polyethylene. Cannula 62 can include an internal or external support structure allowing the position of distal end portion 65 to be adjusted and, thereafter, maintained relative to patient's eye E. To that end, a malleable sleeve 72, for example, can be provided around a portion of distal end portion 65. To limit damage to patient's eye E due to contact with cannula 62, malleable insert 72 is displaced at least two (2) mm from tip T. Malleable insert 72 can be adjusted to move distal end portion 65 and tip T between various positions. When a position is selected, malleable insert 72 serves in maintaining distal end portion 65 and tip T in that position. As such, once distal end portion 65 and tip T are positioned adjacent patient's eye E, cannula 62 can be actuated to supply fluid from reservoir 70 to irrigate patient's eye E.

Figure 4:
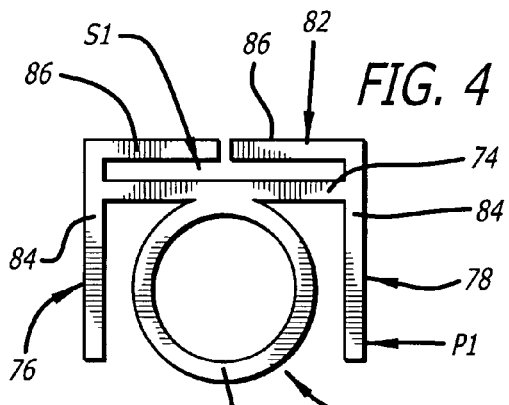
FIG. 4 is a front elevational view of the cannula support shown in FIGS. 1-3.
Figure 5:
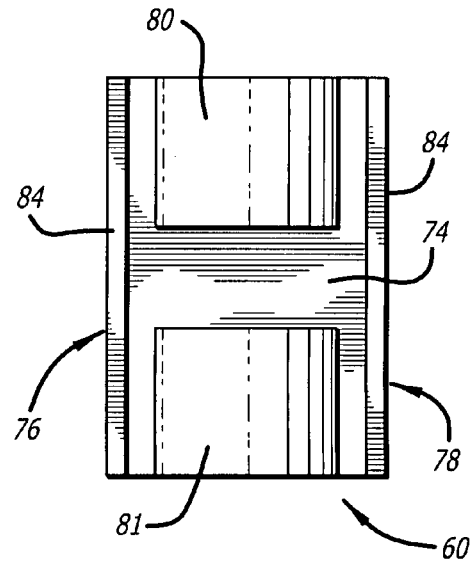
FIG. 5 is a bottom plan view of the cannula support shown in FIGS. 1-4.

FIG. 4 shows cannula support 60 including a base portion 74, and first and second arms 76 and 78. FIG. 5 shows cannula support 60 including first and second cannula holders 80 and 81 to receive a least a portion of cannula 62. Cannula holders 80 and 81 are attached or otherwise secured to base portion 74, and are used to receive cannula 62. Cannula holders 80 and 81 can, for example, be substantially cylindrical tubular members for receiving cannula 62 therein. Although two cannula holders are shown in FIG. 5, more than two cannula holders or as few as one cannula holder can be used to hold cannula 62. Cannula holders 80 and 81 are shown having continuous perimeters, however, one or more cannula holders having interrupted perimeters (FIG. 6) can be used to hold cannula 62.

First and second arms 76 and 78, together with base portion 74, form a gripper 82. Gripper 82 serves in attaching cannula holder 60 to first portion 51 and/or second portion 52 of stem 50. First and second arms 76 and 78 each include first and second arm portions 84 and 86 giving first and second arms 76 and 78 L-shaped cross-sections (FIG. 4). Furthermore, a retention space S1 for receiving a portion of stem 50 is defined between second arm portions 86 and base portion 74, and first arm portions 84 of first and second arms 76 and 78 are pivotably connected to sides of base portion 74.

Figure 4A:
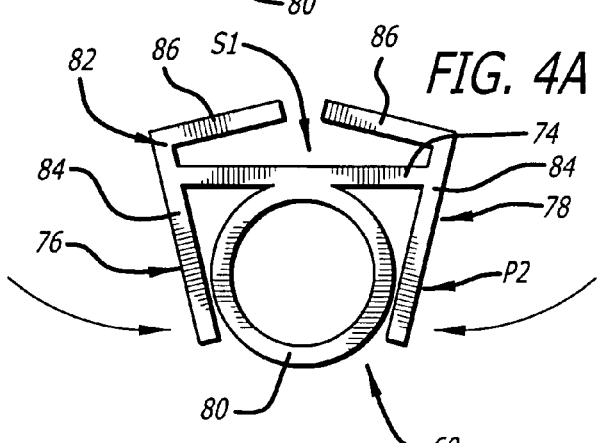
FIG. 4A is a front elevational view of the cannula support of FIGS. 1-3 in another position.

During use of gripper 82, first and second arms 76 and 78 can be pivoted relative to base portion 74 between a first position P1 (FIG. 4) and a second position P2 (FIG. 4A). First and second arms 76 and 78 are biased toward first position P1. Therefore, by pressing inwardly on first arm portions 84, first and second arms can be repositioned from first portion P1 to second position P2. In first position P1, second arm portions 86 are aligned with base portion 74. In second position P2, second arm portions 86 are angled relative to one another and base portion 74 to provide access to retention space S1 for receiving a portion of stem 50 therein. For example, to attach cannula support 60 to stem 50, first portion 51 and/or second portion 52, when first and second arms 76 and 78 are in second position P2, are received in retention space S1. Thereafter, when first arm portions 84 are released, and first and second arms 76 and 78 return to first position P1, retention space S1 closes around first portion 51 and/or second portion 52. In doing so, first and second arms 76 and 78 serve to attach cannula support 60 to stem 50.

Figures 6, 8:
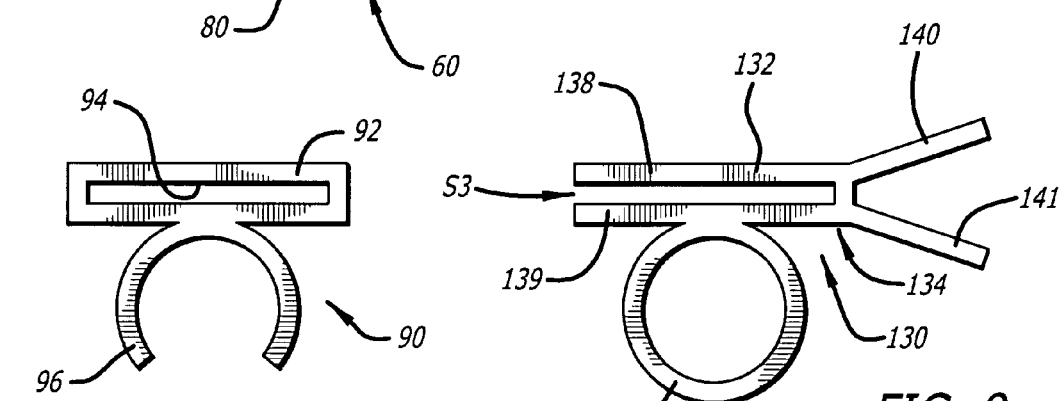
FIG. 6 is a front elevational view of an alternative embodiment of the cannula support of the present invention.
FIG. 8 is a front elevational view of yet another alternative embodiment of the cannula support of the present invention.

FIG. 6 shows an alternative embodiment of the cannula support generally referred to by the numeral 90. Cannula support 90 includes a base portion 92, a cavity 94 formed in base portion 92, and a cannula holder 96 attached or otherwise secured to base portion 92. Cannula holder 96 is used to hold cannula 62 and includes an interrupted perimeter. Although cannula holder 96 can be provided with a continuous perimeter, the interrupted perimeter can in some applications provide increased functionality. For example, when cannula holder 96 is composed of a resilient material, the interrupted perimeter of cannula holder 96 permits cannula 62 to be pressed into position therein by allowing the sidewalls thereof to flex. Furthermore, although one cannula holder 96 is shown in FIG. 6, two or more such cannula holders can be provided to hold cannula 62.

Cavity 94 serves as a gripper for attaching cannula support 90 to stem 50, and is itself a retention space for receiving at least a portion of stem 50. To attach cannula support 90 to stem 50, second portion 52 and then, if necessary, first portion 51 can be inserted into cavity 94. As such, cannula 90 can be attached to stem 50 by receiving first portion 51 and/or second portion 52 in cavity 94. Furthermore, although FIG. 6 shows cavity 94 having a continuous perimeter, a cavity having an interrupted perimeter can be provided.

Figure 7:
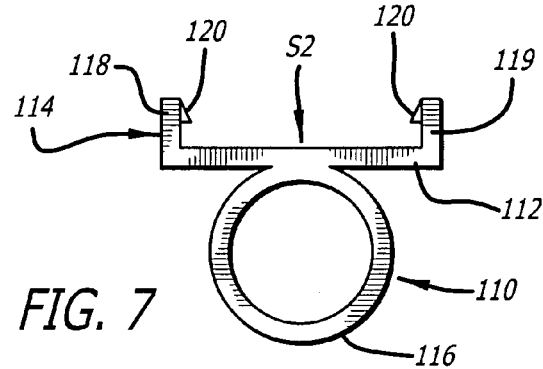
FIG. 7 is a front elevational view of another alternative embodiment of the cannula support of the present invention.

FIG. 7 shows another alternative embodiment of the cannula support generally indicated by the numeral 110. Cannula support 110 includes a base portion 112, a gripper 114, and a cannula holder 116 attached or otherwise secured to base portion 112. Cannula holder 116 is used to hold cannula 62 and includes a continuous perimeter. However, like cannula holder 96, cannula holder 116 can have an interrupted perimeter. Furthermore, although one cannula holder 116 is shown in FIG. 7, two or more such cannula holders can be provided to hold cannula 62.

Gripper 114 comprises base portion 112 and first and second arms 118 and 119, and is used for attaching cannula support 110 to stem 50. Base portion 112 and first and second arms 118 and 119 define a retention space S2 for receiving at least a portion of stem 50. First and second arms 118 and 119 are biased in an initial position (FIG. 7), and are moveable from the initial position to an outwardly deflected position providing access to retention space S2. For example, first and second arms 118 and 119 are formed of a resilient material, and inclined projections 120 are provided on the ends of first and second arms 118 and 119 opposite base portion 112. To attach cannula support 90 to stem 50, first portion 51 and/or second portion 52 are initially contacted against inclined projections 120. Contact of first portion 51 or second portion 52 with inclined projections 120 cause first and second arms 118 and 119 to deflect apart from one another to the outwardly deflected position, and, in doing so, provide access to retention space S3. When first portion 51 and/or second portion 52 are moved past inclined projections 120 and received in retention space S2, first and second arms 118 and 119 return to the initial position, and first portion 51 and/or the second portion 52 are held in position against base portion 112 by inclined projections 120.

FIG. 8 shows yet another alternative embodiment of the cannula support generally indicated by the numeral 130. Cannula support 130 includes a base portion 132, a gripper 134, and a cannula holder 136 attached or otherwise secured to base portion 132. Cannula holder 136 is used to hold cannula 62 and includes a continuous perimeter. However, like cannula holder 96, cannula holder 136 can have an interrupted perimeter. Furthermore, although one cannula holder 136 is shown in FIG. 8, two or more such cannula holders can be provided to hold cannula 62.

Gripper 134 comprises first and second arms 138 and 139, and base portion 132 which is u-shaped. U-shaped base portion 132 includes first and second legs 140 and 141, and a retention space S3 for receiving at least a portion of stem 50 is defined between first and second legs 140 and 141. First and second arms 138 and 139, and first and second legs 140 and 141 are biased in an initial position (FIG. 8), and are moveable from the initial position to deflected positions. First and second arms 138 and 139 are deflectable toward one another, and first and second legs 140 and 141 are deflectable away from one another.

To attach cannula support 90 to stem 50, first portion 51 and/or second portion 52 can possibly be slid into retention space S3. However, first and second arms 138 and 139, and first and second arms 140 and 141 are formed of a resilient material. Therefore, to provide additional access to retention space S3, first and second legs 140 can be moved away from one another to an outwardly deflected position by pinching first and second arms 138 and 139 together. Thereafter, once first portion 51 and/or second portion 52 is received in retention space S3, first and second arms 138 and 139 are released, and first and second legs 140 and 141 return to the initial position, and, in doing so, contact first portion 51 and/or second portion 52.

During surgery, the patient and his or her eye E, as shown in FIG. 1, is positioned within surgery area A along optic axis 18 of surgical microscope 18. Non-contact lens assembly 22 is moved relative to surgical microscope 10 and patient's eye E using positioning assembly 20. In doing so, positioning assembly 20 adjusts the position of non-contact lens B along optic axis 18 to focus surgical microscope 10. Cannula supports 60, 90, 110, and 130 can be attached to stem 50 of non-contact lens assembly 22 before or after non-contact lens assembly 22 is properly positioned relative to surgical microscope 10 and patient's eye E. Cannula supports 60, 90, 110, and 130 serve in fixing the position of at least a portion of cannula 62 relative to non-contact lens assembly 22, and, hence, also surgical microscope 10 and patient's eye E. Malleable insert 72 can then be used to maintain tip T of cannula 62 in close proximity to patient's eye E. Once properly positioned, cannula 62 can be actuated to provided a supply of fluid to irrigate patent's eye E.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A cannula support or supporting a cannula relative to a non-contact lens assembly and a positioning mechanism for positioning the non-contact lens assembly, the cannula support comprising:
    a cannula holder, said cannula holder receiving at least a portion of the cannula; and
    a gripper disposed relative to said cannula holder, said gripper adapted to cooperatively engage a portion of one of the non-contact lens assembly and the positioning mechanism, said gripper having at least one arm depending from said cannula holder, said at least one arm adapted to hold the portion of one of the non-contact lens assembly and the positioning mechanism.

2. The cannula support of claim 1 in combination with a cannula, wherein said cannula can be actuated to release a supply of fluid.

3. The combination according to claim 2, wherein said cannula includes a tip positionable relative to the non-contact lens assembly.

4. The combination according to claim 3, wherein said cannula includes a longitudinal axis, and said tip is formed in a plane non-perpendicular to said longitudinal axis.

5. The combination according to claim 4, wherein said tip is oriented away from the non-contact lens assembly.

6. The combination according to claim 2, wherein said cannula comprises a flexible tube and one of a malleable insert provided therein and a malleable sleeve provided thereon, said flexible tube having a tip, and said malleable insert and said malleable sleeve serving to maintain the position of said tip relative to the non-contact lens assembly.

7. The cannula support according to claim 1, wherein said gripper defines a cavity for receiving one of the non-contact lens assembly and the positioning mechanism.

8. The cannula support according to claim 7, wherein said gripper is moveable between an open position and a closed position, and, when in said open position, said cavity is adapted to receive the portion of one of the non-contact lens assembly and the positioning mechanism.

9. The cannula support according to claim 7, wherein said gripper is moveable between an open position and a closed position, and, when in said closed position, said gripper is adapted to retain the portion of one of the non-contact lens assembly and the positioning mechanism in said cavity.

10. The cannula support of claim 1 in combination with a non-contact lens assembly, wherein the cannula support is attached to said non-contact lens assembly.

11. The combination according to claim 10, further in combination with a microscope adapted for eye surgery and a positioning mechanism for positioning said non-contact lens assembly relative to said microscope.

12. The cannula support of claim 1 in combination with a positioning mechanism, wherein the cannula support is attached to said positioning mechanism.

13. The combination according to claim 12, further in combination with a microscope adapted for eye surgery and a non-contact lens assembly, wherein said positioning mechanism serves in positioning said non-contact lens assembly relative to said microscope.

14. An irrigation system for irrigating an eye during surgery, the irrigation system comprising:
    a cannula; and
    a cannula support comprising a cannula holder, said cannula holder receiving at least a portion of the cannula, and a gripper disposed relative to said cannula holder, said gripper adapted to cooperatively engage a portion of one of a non-contact lens assembly relative the eye, said gripper having at least one arm depending from said cannula holder, said at least one arm adapted to hold the portion of one of the non-contact lens assembly and the positioning mechanism, wherein said cannula can be actuated to release a supply of fluid.

15. A positioning and irrigating system for use during eye Surgery, the system comprising:
    a non-contact lens assembly;
    a positioning mechanism for positioning said non-contact lens assembly relative to the eye;
    a cannula; and
    a cannula support comprising a cannula holder, said cannula holder receiving at least a portion of the cannula, and a gripper disposed relative to said cannula holder, said gripper adapted to cooperatively engage a portion of one of the non-contact lens assembly and the positioning mechanism, said gripper having at least one arm depending from said cannula holder, said at least one arm adapted to hold the portion of one of the non-contact lens assembly and the positioning mechanism, wherein said cannula can be actuated to release a supply of fluid.

16. A surgical microscope assembly for use during eye surgery, comprising:
    a surgical microscope having a focal axis;
    a non-contact lens assembly;
    a positioning mechanism for positioning the non-contact lens along the focal axis;
    a cannula; and
    a cannula support for supporting said cannula, said cannula support being attached to one of said non-contact lens assembly and said positioning mechanism, said cannula support including a gripper having at least one arm depending from said cannula holder, said at least one arm adapted to hold the portion of one of the non-contact lens assembly and the positioning mechanism.

* * * * *